United States Patent
Kirsch et al.

(10) Patent No.: US 11,768,263 B2
(45) Date of Patent: Sep. 26, 2023

(54) MAGNET SYSTEM FOR A MAGNETIC RESONANCE IMAGING SYSTEM

(71) Applicant: Siemens Healthcare GmbH, Erlangen (DE)

(72) Inventors: Rainer Kirsch, Baiersdorf (DE); Stefan Popescu, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 43 days.

(21) Appl. No.: 17/230,934

(22) Filed: Apr. 14, 2021

(65) Prior Publication Data
US 2021/0325493 A1 Oct. 21, 2021

(30) Foreign Application Priority Data
Apr. 17, 2020 (EP) .................................... 20170018

(51) Int. Cl.
*G01R 33/385* (2006.01)
*A61B 5/055* (2006.01)
*A61B 5/00* (2006.01)
*G01R 33/38* (2006.01)

(52) U.S. Cl.
CPC .......... *G01R 33/3854* (2013.01); *A61B 5/055* (2013.01); *A61B 5/4547* (2013.01); *G01R 33/3806* (2013.01)

(58) Field of Classification Search
CPC ............ G01R 33/3854; G01R 33/3806; A61B 5/055; A61B 5/4547
See application file for complete search history.

(56) References Cited

U.S. PATENT DOCUMENTS

| | | | | |
|---|---|---|---|---|
| 4,695,802 A * | 9/1987 | Zijlstra | ................. | H01F 7/0278 324/318 |
| 4,853,636 A * | 8/1989 | Yamamoto | ......... | G01R 33/4833 324/309 |
| 5,337,001 A | 8/1994 | McDougall et al. | | |
| 6,411,187 B1 * | 6/2002 | Rotem | ............... | G01R 33/3806 335/298 |
| 6,600,401 B2 | 7/2003 | Zuk et al. | | |
| 6,954,068 B1 * | 10/2005 | Takamori | ........... | G01R 33/3854 324/318 |
| 7,417,434 B2 | 8/2008 | Overweg | | |
| 7,737,696 B2 | 6/2010 | Overweg | | |
| 2002/0050895 A1 * | 5/2002 | Zuk | ...................... | G01R 33/383 335/216 |

(Continued)

FOREIGN PATENT DOCUMENTS

EP 3828573 A1 6/2021

OTHER PUBLICATIONS

Partial EP Report for German Application No. 20170018.4 dated Oct. 7, 2020.

(Continued)

*Primary Examiner* — Dixomara Vargas
(74) *Attorney, Agent, or Firm* — Banner & Witcoff Ltd.

(57) ABSTRACT

The disclosure describes a magnet system for a magnetic resonance imaging system comprising a basic field magnet and a gradient system, wherein coils of the gradient system are positioned outside the area of a predefined basic magnetic field (B0) of the basic field magnet. The disclosure further describes a gradient system and a magnetic resonance imaging system with such a magnet system.

11 Claims, 6 Drawing Sheets

(56) References Cited

U.S. PATENT DOCUMENTS

| | | | |
|---|---|---|---|
| 2002/0123681 A1* | 9/2002 | Zuk | A61B 5/055 600/410 |
| 2004/0106865 A1 | 6/2004 | Schuster et al. | |
| 2006/0261813 A1 | 11/2006 | Schuster et al. | |
| 2007/0108979 A1* | 5/2007 | Ryan | G01R 33/3815 324/318 |
| 2007/0216409 A1* | 9/2007 | Overweg | G01R 33/385 335/297 |
| 2010/0056378 A1* | 3/2010 | Timinger | G01R 33/3815 324/322 |
| 2010/0069738 A1* | 3/2010 | Timinger | G01R 33/3815 324/315 |
| 2010/0226058 A1* | 9/2010 | Blakes | H01F 6/02 361/143 |
| 2010/0267567 A1* | 10/2010 | Overweg | G01R 33/3815 335/216 |
| 2012/0288820 A1* | 11/2012 | Choe | A61B 5/682 433/29 |
| 2014/0111202 A1* | 4/2014 | Wald | G01R 33/383 324/309 |
| 2014/0145721 A1 | 5/2014 | Nowak | |
| 2014/0274721 A1* | 9/2014 | Calvert | G01R 33/3854 324/309 |
| 2015/0084631 A1* | 3/2015 | Bradshaw | G01R 33/3875 324/318 |
| 2015/0177343 A1* | 6/2015 | Wald | G01R 33/46 324/309 |
| 2015/0346294 A1* | 12/2015 | Nogami | G01R 33/34 324/322 |
| 2018/0199853 A1 | 7/2018 | Abkai et al. | |
| 2020/0305758 A1* | 10/2020 | McDaniel | G01R 33/3808 |
| 2020/0355764 A1* | 11/2020 | Popescu | G01R 33/5608 |
| 2020/0355771 A1* | 11/2020 | Popescu | G01R 33/32 |
| 2021/0156936 A1* | 5/2021 | Popescu | A61N 5/1065 |
| 2021/0156937 A1* | 5/2021 | Popescu | G01R 33/381 |
| 2021/0156941 A1* | 5/2021 | Popescu | G01R 33/56572 |
| 2021/0341556 A1* | 11/2021 | Mallett | G01R 33/383 |
| 2022/0236349 A1* | 7/2022 | Van Lanen | H01F 6/06 |

OTHER PUBLICATIONS

Extended EP Report for German Application No. 20170018.4 dated Jan. 18, 2021.

* cited by examiner

14 - Sequence control unit
15 - Radio-frequency transmission device
16 - Gradient system interface
17 - Radio-frequency reception device
18 - Reconstruction unit
19 - Memory

MAGNET SYSTEM FOR A MAGNETIC RESONANCE IMAGING SYSTEM

CROSS-REFERENCE TO RELATED APPLICATIONS

The present application claims the benefit of the filing date of European patent application no. EP 20170018.4, filed on Apr. 17, 2020, the contents of which are incorporated herein by reference in their entirety.

TECHNICAL FIELD

The disclosure relates to a magnet system, such as a gradient system for magnetic resonance imaging (MRI), which may be implemented for dental and extremity MRI scanners.

BACKGROUND

For more than four decades, the principle of magnetic resonance imaging ("MRI") has been used for imaging and other measurements. In simplified terms, for this purpose, the object under examination is positioned in a magnetic resonance (MR) scanner in a comparatively strong and homogeneous static magnetic field, also known as the B0 field, having a field strength of 0.2 T to 7 T, such that the nuclear spins of the object orient along the static magnetic field lines. In order to trigger the nuclear spin resonances, high-frequency excitation pulses (HF pulses or radio-frequency (RF) pulses) are irradiated toward the object under examination. The measured nuclear spin resonances is called k-space data, and it is used for the reconstruction of MR images or the calculation of spectroscopy data.

For spatial encoding of the measured data, dynamically switching magnetic gradient fields are superimposed on the static magnetic field. The recorded measured data is digitized and stored into a k-space matrix as complex values. An associated MR image can be reconstructed from the k-space matrix populated with such values, for example by means of a multidimensional Fourier transformation.

Traditional MR scanners employ a solenoidal type superconducting magnet while the patient is placed inside the bore of the MR scanner during the imaging session. Such scanner design confines the patient within a tight space and limits the accessibility to the patient's body for the medical staff, e.g. to carry out an interventional or therapeutic procedure guided by real-time MR imaging.

Most prior art of dental MR scanner employs solenoid type magnets that tend to be of large outer diameter due to the need to integrate an outer active shielding coil for safe operation within a dentist office, e.g. as it is shown in US 2018/0199853 A1. Moreover, and as the imaging field of view is positioned deeply into the central inner region of the solenoid, the access of the patient head into the magnet bore is further restricted by a cylindrical gradient coil positioned inside the magnet bore. The end effect is that the magnet inner bore shall be large enough to allow for access of the patient shoulders. This solution largely increases the scanner size and also the costs.

Other scanner architectures use a C-shaped basic field magnet with an examination area lying between the two magnet shoes of the magnet. More recently, a new scanner architecture is introduced comprising a toroidal basic magnetic field and multiple examination areas between magnet coils producing the toroidal magnetic field.

SUMMARY

Looking at all these scanner architectures noted above, they all have in common that they comprise gradient coils that are always positioned inside the basic magnetic field. The functional structure of these known systems can be compared with a Russian nesting doll: In the middle there is the patient or the examination area that is "surrounded" by coils for emitting and receiving radio frequency (RF), and in the next "sphere" there are arranged the gradient coils that are enclosed by the basic field magnet.

Regarding gradient coils, their shape is adapted to the basic magnetic field. There are solenoids and also planar coils that can be arranged parallel or in a V-shape. However, often the shape of the basic field magnetic seriously limits the space available for fitting the gradient coils around the examination area. As the gradient coils are very close to the field-of-view (FOV, i.e. the zone of an examination area) and the gradient coil size is restricted by the need to keep the magnet size as small as possible, a problem results with the attainable linearity of the gradient fields over the extension of the imaging region. Another serious drawback of the known scanner architecture is the acoustic noise that is generated by the gradient coils during measurement.

It is the object of the embodiments described in the disclosure to disclose a new design for a dedicated MR scanner architecture, e.g. for imaging specific organs or part of the human body, for example the dentition of a patient, that offers better gradient fields on the one hand and generates lower acoustic noise levels on the other hand.

This object is achieved by a magnet system according to embodiments described in the disclosure including the claims, and as further discussed below includes a gradient system according and a magnetic resonance imaging system.

A magnet system according to an embodiment of the disclosure for a magnetic resonance imaging system comprises a basic field magnet and a gradient system (with gradient coils). These gradient coils may be pairs of coils of the gradient system that are used to generate a gradient field for an axis of the gradient system. The coils of the gradient system should be positioned outside the area of the predefined basic magnetic field of the basic field magnet. It is yet clear that the basic field magnet is designed to apply the predefined basic magnetic field in a predefined examination area during an examination, and that the gradient coils are designed and positioned to apply a gradient field in this examination area during this examination. Not all coils of the gradient system have to be outside the area of the basic magnetic field, however, but at least the gradient coils should be arranged outside this area.

A magnet system according to an embodiment of the disclosure for a magnetic resonance imaging system comprises a number of pairs of gradient coils. This means that there are two gradient coils for each gradient axis. Typically, the gradient system creates gradients in X, Y, and Z direction to realize a gradient distribution having X, Y, and Z components. Thus, it is preferred that there is a pair of X gradient coils, a pair of Y gradient coils, and a pair of Z gradient coils. It is clear that two gradient coils designed to create the same gradient (and being arranged on opposite sides of an examination area) form a pair. The gradient coils of each pair (i.e. the X, Y, and/or Z gradient coils) are arranged at opposite sides of an examination area. The examination area is the area where within the imaging process takes place, i.e. the volume enclosing the field of view (FOV) of the scanner.

Surely, the gradient system could also comprise further components that the gradient systems of the state of the art also comprise for an optimal functioning. These are e.g. dedicated gradient power amplifiers for each axis GPAx, GPAy, and GPAz or holding structures. Also, the gradient system may comprise further coils, e.g. shim coils, coils generating non-linear encoding fields or dynamic field cycling coils for multi-dimensional spatial signal encoding and accelerated signal acquisition. While it is preferred that at least the gradient coils are arranged outside the basic magnetic field, since their wires carry the strongest and fast switching electric currents, it is also an option to arrange the other coils as well outside the basic magnetic field.

The "predefined magnetic field" of the basic field magnet is the field used for measurements. Since magnetic fields are always circulating in a closed-path (and extend to infinity), it is not easy to define an inside and outside of a magnetic field if looking at it in a meticulous manner. However, a person skilled in magnetic resonance imaging can easily divide the basic magnetic field in a main field that lies in the examination area that is used for measurements and a stray field lying outside the examination area. The "main field" is the predefined basic magnetic field mentioned above. The other part of the magnetic field will be designated as the "stray field".

The expression "outside" means that at least the proportion of the basic magnetic field used for measurements (the field lines running through the examination area/imaging volume) is not penetrating the respective gradient coils. Thus, respective gradient coils are arranged such that e.g. no field lines of the basic magnetic field (main field) that are directly involved with the measurements are running through these gradient coils. Depending on the shape of the basic field magnet, one could also say that the respective gradient coils are not arranged in a space between the basic field magnet generator and the examination area. Alternatively, looking at a C-shaped basic field magnet one could say that there is at least one pole shoe (e.g. piece) of each polarity of a magnet lying inside a gradient coil or that the pole shoes (e.g. pieces) are lying between the gradient coils (depending on the shape of the gradient coils). Looking at a solenoid basic field magnet, the gradient coils are arranged outside the solenoid coil. Looking at the stray field, one could say that the respective gradient coils are arranged in the stray field. Looking at absolute values of the field strength, "outside" means that the respective gradient coils are arranged in an area where the (predefined) field strength of a (stray) field applied by the basic field magnet generator is less than 10% of the (predefined) field strength in the examination area or the maximum field strength of the basic field magnet, preferably less than 1%, especially less than 0.1%.

The above described arrangement of the coils of the gradient system has the advantage that the basic field magnet can be designed smaller, which has a positive effect on the homogeneity of the basic magnetic field and the costs of the magnet. Furthermore, the acoustic noise level generated during examination is reduced. The noise level that occurs during the examination is proportional to the Lorenz forces acting on gradient coil conductors, which can be described by the formula $F=q \cdot v \times B$. (F=force on the conductors of the gradient coil, $q \cdot v$=current that flows through the conductors of the gradient coil, B=strength of the magnetic field in which the conductors of the gradient coil are perpendicular to the magnetic field).

In the case of open magnetic resonance scanners that have pole pieces (e.g. C-shaped magnets), the basic magnetic field lies between the pole pieces. The solution to the problem (volume) is solved by installing the gradient coils with an open magnetic resonance scanner outside the primary magnetic field according to the embodiments of the disclosure. This also reduces the force acting on the conductors and thus the resulting mechanical vibrations and acoustic noise.

In order to keep the linearity of the magnetic gradient fields as high as possible by minimizing the cross-product terms (Maxwell terms) and the high-order terms it would be required to increase the size of the gradient coils to be at least twice larger that the imaging volume and also to locate these coils away from the imaging region at a comparable distance. This can be achieved by the embodiments of the present disclosure, since the size of the gradient coils is not restricted by the geometry of the basic field magnet.

With gradient coils located within the magnet, conventionally an enlargement of the gradient coils would result in increasing the size of the magnet. A larger magnet size involves a higher production cost, which scales with the 3rd power of the magnet outer diameter. A larger magnet size results in a larger footprint for the extension of the stray magnetic fields (this is the 5G safety contour line). A larger footprint means higher installation costs at the customer site and restricted clinical workflow due to safety regulations. Thus, the embodiments of the disclosure have an advantageous effect on many aspects of an MRI system.

Thus, the new architecture places the gradient coil pairs outside the basic field magnet with the main benefit that the linearity of the generated magnetic gradient fields can be maximized at least inside the FOV, while the geometry of the magnet can be optimized to fit the target anatomy. Thereby the size and finally the cost for the main magnet (basic field magnet) can be greatly reduced for the same spatial extension of the imaging volume (examination area). As the prior art places the gradient coils inside the magnet torus, it thereby increases the size and the cost of the magnet. Furthermore, the disclosure allows a better access of medical staff to the patient for conducting clinical intervention and therapeutic procedures.

A gradient system according to an embodiment of the disclosure for a magnet system according to the disclosure comprises coils of a gradient system that are designed to be arranged outside a predefined area of a magnetic field of a basic field magnet.

A magnetic resonance imaging system according to the disclosure comprises a magnet system according to the disclosure. A preferred MR scanner architecture is particularly suited for MR imaging of dedicated body parts or organs of a patient (human or animal). Since the gradient system is arranged outside the basic magnetic field, the size of the basic field magnet can be chosen depending on the organs to be imaged with the system. The magnetic resonance imaging system may be designed for examining the head, the prostate, extremities, animals, neonates, and may be designed for dental imaging and/or designed for an examination of a body part of the group comprising brain, wrist, elbow, foot, ankle, knee, breast, prostate, etc. of a patient.

In an embodiment, the magnetic resonance imaging system comprises at least one examination area, e.g. two or more examination areas, and the gradient system according to an embodiment of the disclosure for at least one examination area. A MRI-scanner of such magnetic resonance imaging system comprises an inclined arrangement of basic field magnets, e.g. a star-shaped arrangement. MRI scanners with a toroidal MR scanner architecture may be particularly advantageous. In a star shaped arrangement of basic field magnets with a toroidal magnetic field, the front side of the gradient system should point to the outside of the toroid magnetic field.

Particularly advantageous embodiments and features of the disclosure are described herein and recited in the disclosure including the claims, as revealed in the following description. Features of different categories (e.g. methods, apparatuses, systems, etc.) may be combined as appropriate to yield further embodiments not described herein.

In an embodiment, a magnet system may provide the coils positioned outside the area of a predefined basic magnetic field of the basic field magnet are gradient coils, e.g. gradient coils for all three coordinate axes. Alternatively or additionally, the coils positioned outside the area of a predefined basic magnetic field of the basic field magnet are shim coils and/or coils generating non-linear encoding fields and/or dynamic field cycling coils for multi-dimensional spatial signal encoding and accelerated signal acquisition. In an embodiment, the additional coils are arranged parallel to the gradient coils, e.g. wherein the gradient system comprises blocks of coils comprising gradient coils and other coils. Since the gradient coils are arranged outside the basic magnetic field between the two magnet shoes, there will be a strongly reduced noise emission that can be diminished below the hearing threshold depending on the arrangement of the gradient coils outside the basic magnetic field.

In an embodiment, a magnet system may provide the basic field magnet as a C-shaped magnet and coils of the gradient system, e.g. gradient coils, are arranged in the region of a pole shoe of the basic field magnet or such that the pole shoes of the basic-field-magnet lie between two of these coils.

In an embodiment, a magnet system may provide the basic field magnet having a toroidal field distribution and e.g. two or more examination areas. The basic field magnet coils may be arranged in a star shape. One advantage of using toroidal magnet systems for MRI scanners is that such magnet configurations minimize the stray field and eliminate the need for active shielding coils, which makes these magnets also even more efficient and cost effective. This allows compact siting of the MRI scanners, possible directly in the doctor's office without having to install them in a separate examination room.

Thus, according to an embodiment, the basic field magnet arrangement comprises at least one group of basic field magnet segments (coils or groups of coils), which are arranged in a star shape around at least one spatial axis, with a side wall or edges of the respective basic field magnet segment pointing to this central axis. This arrangement may be rotationally symmetrical, with rotational symmetry of 360°/N for example being particularly advantageous for N basic field magnet segments (in a group). With six basic field magnet segments, the basic field magnet arrangement would be e.g. like a six-pointed star. However, a star shape can also include another (partially) regular arrangement of magnet segments, e.g. that the basic field magnet segments are all regularly arranged within a semicircle. An arrangement of several of these partially regular star shapes around several central axes or spatial axes, e.g. two semicircular arrangements that are slightly spaced apart to make a total of e.g. to generate the above-mentioned basic magnetic field in the form of a toroid with straight passages inserted.

In an embodiment a magnet system may provide the basic field magnet comprising an (iron) magnet yoke and coils of the gradient system arranged such that their field couples into the magnet yoke. Thus, both, the basic field magnet and the coils of the gradient system may use the same yoke. The distance between the magnet yoke and each of the respective coils of the gradient system (arranged out-side the basic magnetic field) may be less than 2 cm, e.g. when the respective coils are in contact with the magnet yoke. Due to this small gap, a coupling of the magnetic field of the coils into the yoke is much more effective than with a larger gap between the coils and yoke.

In an embodiment, a magnet system may provide the coils of the gradient system as planar coils e.g. in a parallel arrangement. The parallel arrangement compared to a V-shaped arrangement can be an advantageous architecture that allows for achieving a better linearity of the gradient fields given relaxed design restrictions. These degrees of freedom can be further leveraged for minimizing the peripheral nerve stimulation effects and the generation of undesired eddy currents. According to a gradient system embodiment, the gradient coils are bi-planar gradient coils. This has the advantage that the gradient system does not need much space. The gradient system may comprise two or three pairs of gradient coils (e.g. X, Y and Z gradient coils), wherein all pairs of gradient coils are arranged in the same angle to another, i.e. the angle between the central planes are equal.

In an embodiment, a magnet system provides the coils of the gradient system being placed symmetrically related to an examination area inside the predefined basic magnetic field of the basic field magnet. The respective coils may be arranged with a distance to another so that an object to be examined or the examination area fits between the respective coils. For example, in the particular case of dental imaging, such a solution allows for the patient head to fit inside the space in between gradient coils.

In an embodiment, a magnet system provides coils of the gradient system as mechanically decoupled from the magnet, e.g. wherein the coils are movable relative to the basic field magnet, especially by an actuator arm. In an example geometry, the gradient coils are mounted so that they can be rotated at an angle around the Z-axis. This allows to fit the gradient coils closer to the head and to avoid mechanical collisions with the patient shoulders. For example, the gradient coils are mechanically decoupled from the magnet and can be independently lifted-out by the actuator arm during the non-imaging time and relocated away from the patient body. This approach offers better access to the patient for the medical staff, as it may be often required for operative or non-operative dentistry or orthopedic procedures.

In an embodiment, a magnet system provides the basic field magnet arranged between coils of the gradient system, wherein the distance between these coils is e.g. larger than the dimensions of the basic field magnet. This allows a minimal size of a basic field magnet.

In an embodiment, a magnet system provides the basic field magnet shaped such that it fits the target anatomy, e.g. wherein the basic field magnet is shaped like an open segment of a torus or cylinder for examination of extremities or shaped like a bicycle seat or a saddle for prostate exams With the gradient system outside the basic field magnet, the scanner architecture can be easily modified to fit other body parts and internal organs, like for example for imaging the wrist, the elbow, the knee, the foot and foot-ankle, the female breast or the male prostate. The new architecture will be further appropriate for scanners dedicated to image a variety of small animals for veterinary applications. The scanner architecture may be also used for imaging neonates having the major advantage of only weak acoustic noise generated by the operation of gradient coils.

An advantage for all these various scanner configurations is that the magnet used to generate the static magnetic field can be made of the smallest possible size (and thereby of lowest possible cost and with the smallest footprint concerning the stray field) and shaped such that to optimally fit the target anatomy whilst the gradient coil system may be larger and designed to allow easy access to patient body for interventional procedures and to allow unrestricted positioning of the patient within the scanner.

In an embodiment, a magnet system provides the gradient system comprises a cooling system that is also arranged outside the area of a predefined basic magnetic field of the basic field magnet. Furthermore, the embodiments as described herein offer the general advantage that it is not absolutely necessary to shield the gradient coils, what makes them more efficient and heat dissipation is lower. Forced cooling for the gradient coils may be nevertheless advantageous. With the above described embodiment, a cooling solution will neither interfere mechanically with the basic field magnet nor restrict its geometry. With the embodiment described herein, and especially the present embodiment, the heat developed within the gradient coils would mostly not be transferred to the magnet, thereby resulting in thermal drift of the magnet field intensity or its spatial distribution, whereas the heat sources in gradient coils will not be closely located or radiating toward the patient body.

In an embodiment, a magnet system provides the gradient coils arranged in a pivotable way, e.g. such that that they can be moved like a door, e.g. wherein the gradient coils are planar coils and especially comprising a full faced cover so that they are designed to act as a blind. This is especially advantageous for a star shaped arrangement of basic field magnets or other arrangements with multiple examination areas, since it may be necessary to arrange the coils of the gradient system for a first examination area in front of a second examination area. These coils could be blocking the second examination area, and it should be possible to open the coils like doors for the second examination area. However, when the coils are used like doors, they may also be used as blinds to block the view into the second examination area. A star shaped arrangement of examination areas could be surrounded by coils of the gradient system, which could all be used as doors and/or blinds in addition to their technical use.

Since coils of the gradient system are positioned outside the basic field magnet and their orientation could be bound to mechanical constraints of the magnetic resonance imaging system, it could occur that their windings have to be adapted in order to produce an optimal gradient field.

In an embodiment, a gradient system provides a gradient coil formed by a plurality of loops of a conductor. It is clear that e.g. only one long conductor is wound into a number of loops, however, there could also appear open loops that are connected to another. In the following, the loops of a coil are designated as a "set of loops", wherein any references to moving actions are meant to be understood as changes of following loops. The following designs are examples and may constitute additional or alternate designs that may be combined with one another and/or the various embodiments described herein:

The loops of a gradient coil for the X-gradient comprise two sets of contra-rotating loops adjacent in X-direction, e.g. wherein the radius of a set of loops increases, with the outer conductors in X-direction (the front and the back side) essentially remaining at the sides of the gradient coil. This means that the shape of such coil reminds one of a butterfly.

The loops of a gradient coil for the Y-gradient comprise two sets of contra-rotating loops adjacent in Y-direction, e.g. wherein the radius of a set of loops increases, with the outer conductors in Y-direction essentially remaining at the sides of the gradient coil (the sides perpendicular to the front and the back side). This means that the coil may look as the coil for the X gradient only rotated 90°.

The loops of a gradient coil for the Z-gradient comprise a set of increasing loops, e.g. wherein the center of the loops essentially remain in the center of the gradient coil. This means that the coils may be coaxial but growing bigger, at least in X-direction.

In the following, additional special designs of coils are described. These special designs result in a field that increases in the direction of the mouth of a V-shape (to the front side) of the gradient system.

Regarding the gradient coil for the X-gradient, the distance of the field-relevant conductors of a set of loops steadily decreases at least in the direction of the aperture of the V-shape (in direction to the front side) of the gradient system. The field relevant conductors are these part of the loops that determine the magnetic field of a gradient.

Regarding the gradient coil for the Z-gradient, the distance of the field-relevant conductors of a set of loops steadily decreases at least in the direction of the aperture of the V-shape (in direction to the front side) of the gradient system.

Regarding the gradient coil for the Y-gradient, the radius of a set of loops increases in X-direction as well as in Y-direction with the outer conductors at the aperture of the V-shape essentially remaining at the side of the aperture (i.e. at the front side) as well as at the sides perpendicular to the front side.

Various hardware or software tools can be used to further fine-tune these wire patterns in order to meet any suitable additional constrains such as the gradient linearity, to reduce the stray fields, the amplitude of mechanical vibrations and the level of acoustic noise or peripheral nerve stimulation, etc.

Special loop-shaping as described may eliminate non-linear components along the X-axis for the X and the Z gradient coils by modifying the wire spacing along the X-axis from a constant one to a more quadratic one, with the wire density increasing approximatively quadratically with the radial distance to the axis of symmetry (e.g. of a toroid basic magnet). For the Y gradient coils, an exemplary solution adds an additional wire distribution having constant spacing along the X-axis. This is similar to the wire patterns for the magnet coil used for generating the static magnetic field B0.

A method in accordance with the embodiments described herein has the additional advantageous effect that it can be used for compensating stray magnetic fields in a magnetic resonance imaging system with two or more examination areas. The method comprises the following steps:

providing a value for a predefined gradient field to be applied in a first examination area, in addition to a basic magnetic field, providing a predefined sequence control pulse to be applied in a second examination area (especially adjacent to the first examination area, since the effect is strongest in adjacent areas), determining a stray magnetic field in the second examination area in the case the gradient field is applied in the first examination area, calculating a compensated sequence control pulse for the second examination area from the predefined sequence control pulse and the determined stray magnetic field, wherein the compensated sequence control pulse is calculated such that a measurement in the second examination area can be performed despite the stray field, and applying the compensated sequence control pulse to the second examination area and—preferably repeating these steps for a further examination area, especially for all examination areas.

The value for the gradient field that is used to be applied in the first examination area is well known. When applied in the first examination area, this gradient field produces stray fields in the other examination area(s).

The stray fields affect measurements in a second examination area. If the second examination area is adjacent the first examination area (wherein this case is preferred, since the stray field is strongest in adjacent areas), the disturbance of a measurement by the stray magnetic field is severe. For a measurement, a predefined sequence control pulse is applied in the second examination area, wherein this predefined sequence control pulse is e.g. a predefined second gradient field. Since the stray field affects a measurement with this sequence control pulse, this sequence control pulse is adjusted to the stray field with the following steps.

The information defining a predefined sequence control pulse are data about the strength and the direction of the sequence control pulse. Since in an MRI system there are defined gradient magnet coils, the data may comprise information about a signal-amplitude or a current and the coil or antenna where this signal is to be applied.

It should be noted that in all examination areas of the MRI system the influences of stray magnetic fields should be compensated. Thus, e.g. values for predefined sequence control pulses of all examination areas should be provided and the method should be performed on all examination areas while regarding any examination area as first area and any other examination area as second examination area.

Before, during, or after providing any information about a predefined sequence control pulse, there is determined the stray magnetic field in the second examination area, e.g. its direction and its strength (magnetic field vector). This is the stray magnetic field of the gradient field. This step can be achieved by calculating or by measuring the stray magnetic field.

For example, the gradient field could be applied in the first examination area and the stray magnetic field can be measured in the second examination area (e.g. for different currents inducing the gradient field). The measured values can be stored and used for the determination of the stray magnetic field in the second examination area for the case that the gradient field is applied in the first examination area (with a predefined current). However, if the properties of the MRI-scanner are well known, the magnetic field can also be calculated (e.g. in a simulation). Last, for a group of identical MRI-scanners, a set of stored values can be used for the determination.

Using the determined stray magnetic field, and the provided (predefined) sequence control pulse, a compensated sequence control pulse can be calculated for the second examination area. This compensated sequence control pulse can be determined directly, or a correction term can be calculated and added to or subtracted from the predefined sequence control pulse. Since the direction of the predefined sequence control pulse and the stray field may be important, it may be an option to calculate a resulting compensated vector from a vector representing the predefined sequence control pulse and a correction vector (based on the stray field).

After that, the compensated sequence control pulse is applied to the second examination area. This application is well known and the compensated sequence control pulse is applied instead of the predefined sequence control pulse.

This solution allows an active compensation of the stray gradient fields at least in the first order. With his compensation it is possible to simultaneously and independently acquire images in different examination areas, wherein in each examination area there may operate a dedicated three-axis gradient system. A compensation of stray fields up to the first order is adequate if the target field of view is not too large and the active shielding of the gradient coils is reasonably effective. Nevertheless, this method can be extended to correct for higher order stray fields. This would e.g. require a set of dynamic higher-order shim coils and associated coil current amplifiers, and correspondingly a larger sensitivity matrix to invert. The higher order compensation is explained further below.

Although the disclosure is very advantageous for star-shaped magnet arrangements, it is also advantageous for other MRT-systems with e.g. a linear arrangement of examination areas or an arrangement of "satellite examination areas" using the basic magnetic field of a central examination area.

In an embodiment, a magnetic resonance imaging system provides the magnetic resonance imaging system designed such that the gradient systems in an examination area, e.g. in each examination area, operates asynchronously and/or independent of the gradient system in another examination area of the magnetic resonance imaging system.

As an example, the gradient system comprises a central control unit that is designed to coordinate all gradient activities, e.g. the independent operation of different gradient systems, especially even the minimization and/or the correction of cross-interference terms between the gradient systems. The term "working independently" means that the MR sequences running in the examination regions are not necessarily identical or synchronized or interleaved.

The magnet architecture according to an embodiment of disclosure comprises the advantage that, especially in combination with a toroidal magnet having a relatively weak stray magnetic field outside the torus, the gradient coils are acoustically quiet. This results from the fact that, unlike the prior art that places the gradient coils in regions of strong magnetic field, the new solution exposes the wires of the gradient coils at significantly weaker static magnetic field, i.e. actually only to the stray field. As a result, the Faraday forces acting upon these wires operated by strong currents pulses are significantly lower, and thus the mechanical vibrations and the resulting acoustic noise are of much lower amplitudes.

In addition, it is advantageous that the size of the coils of the gradient system is not restricted anymore, therefore it is possible to implement gradient coils for all three coordinate axes as well as further coils generating non-linear encoding fields or dynamic field cycling coils for multi-dimensional spatial signal encoding and accelerated signal acquisition.

BRIEF DESCRIPTION OF THE DRAWINGS/FIGURES

Other objects and features of the embodiments of the present disclosure will become apparent from the following detailed descriptions considered in conjunction with the accompanying drawings. It is to be understood, however, that the drawings are designed solely for the purposes of illustration and not as a definition of the limits of the disclosure. In the drawings, identical components are indicated using identical labels. In the diagrams, like numbers refer to like objects through-out. Objects in the diagrams are not necessarily drawn to scale. Further advantages, features and details of the disclosure will emerge from the exemplary embodiment described below and from the associated drawings in which:

DETAILED DESCRIPTION

Figure 1:
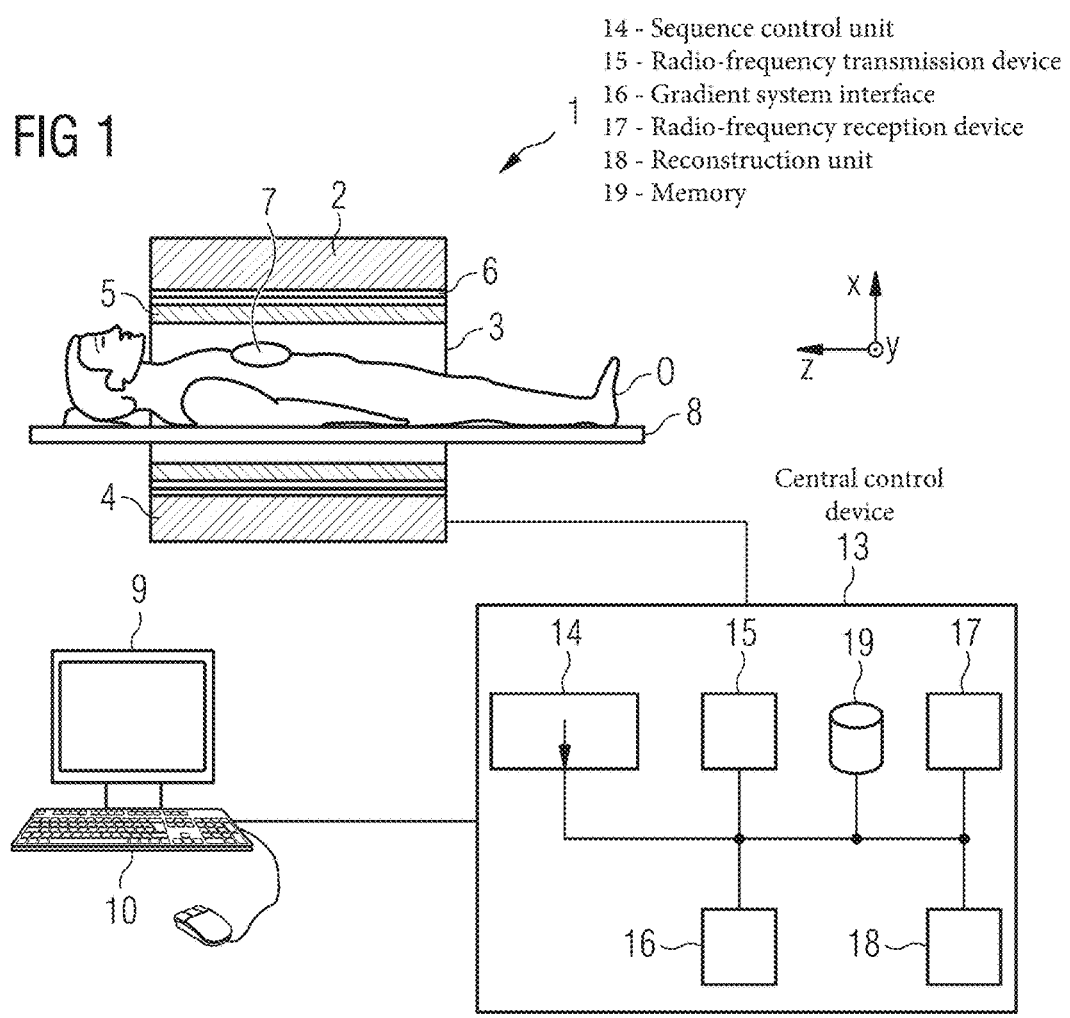
FIG. 1 shows a simplified MRI system of the state of the art.

FIG. 1 shows a schematic representation of a magnetic resonance imaging system 1 ("MRI-system"). The MRI system 1 includes the actual magnetic resonance scanner (data acquisition unit) 2 with an examination space 3 or patient tunnel in which a patient or test person is positioned on a driven bed 8, in whose body the actual examination object O is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils 6x, 6y, 6z, (see following figures) to switch (activate) gradients in the x-direction, y-direction, or z-direction independently of one another.

The MRI system 1 shown here is a whole-body system with a patient tunnel into which a patient can be completely introduced. However, in principle the disclosure can also be used at other MRI systems, for example with a laterally open, C-shaped housing, as well as in smaller magnetic resonance scanners in which only one body part can be positioned.

Furthermore, the MRI system 1 has a central control device 13 that is used to control the MRI system 1. This central control device 13 includes a sequence control unit 14 for measurement sequence control. With this sequence control unit 14, the series of radio-frequency pulses (RF pulses) and gradient pulses can be controlled depending on a selected pulse sequence.

To output the individual RF pulses of a pulse sequence, the central control device 13 has a radio-frequency transmission device 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device 17 (likewise communicating with the sequence control unit 14 in a suitable manner) to acquire magnetic resonance signals (i.e. raw data) for the individual measurements, which magnetic resonance signals are received in a coordinated manner from the RF reception antenna system 7 within the scope of the pulse sequence.

A reconstruction unit 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI system 1 can thus also be operated by an operator. MR images can also be displayed at the display unit 9, and measurements can be planned and started by means of the input unit (e.g. in combination with the display unit 9), and in e.g. suitable control protocols can be selected (and possibly modified) with suitable series of pulse sequence PS as explained above.

The MRI system 1 may have a number of additional components that are not shown in detail but are typically present at such systems, for example a network interface to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
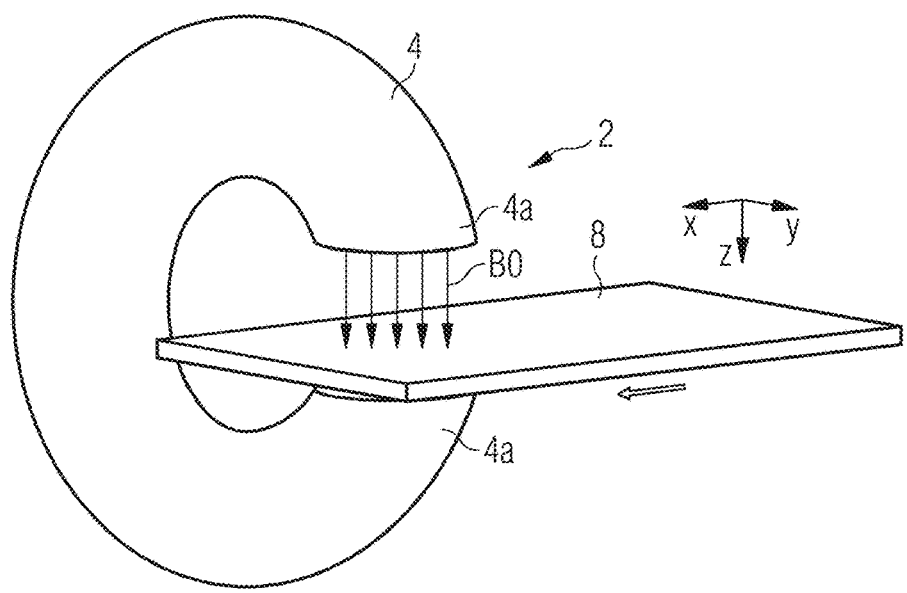
FIG. 2 shows a simplified C-shaped MRI scanner of the state of the art.

FIG. 2 shows a simplified C-shaped MRI scanner 2 of the state of the art. The general setup of a respective MRI-system is similar to FIG. 1 with the difference that the scanner 2 now comprises a C-shaped basic field magnet 4 as shown in this figure. A theoretical coordinate system is shown, where the z-axis points in the direction of the basic magnetic field B0 and the x- and y-axis are perpendicular to another and both perpendicular to the z-axis.

A body part of a patient (see e.g. FIG. 3) is arranged in the gap between the two magnet shoes 4a of the basic field magnet 4. The patient may lie on the bed 8 or stand upright as it may be derived from FIG. 3.

Figure 3:
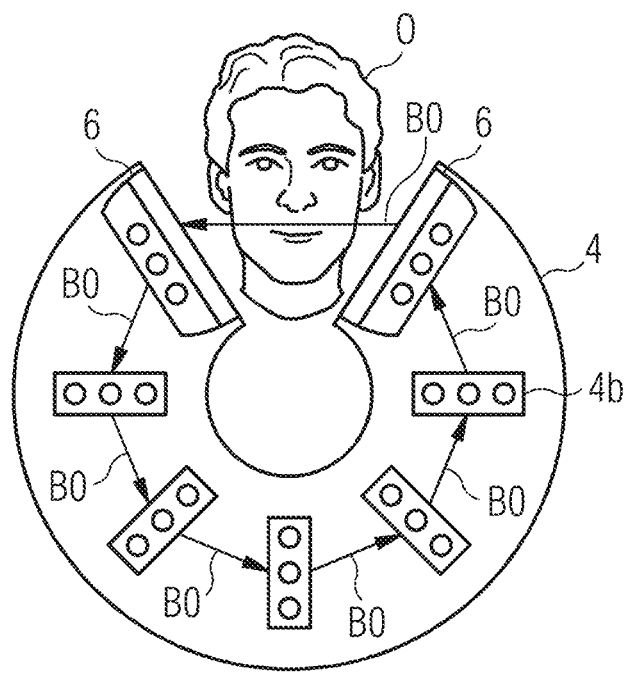
FIG. 3 shows an examination in a C-shaped MRI scanner of the state of the art.

FIG. 3 shows an examination in a C-shaped basic field magnet 4 of an MRI scanner 2 (see e.g. FIG. 2) of the state of the art. The scanner architecture uses a planar V-shaped gradient system 6.

This solution seriously limits the space available for fitting the gradient system 6 inside the torus of the basic field magnet 4 in the line of its magnet coils 4b and the acoustic noise level is high. In addition, since the gradient system 6 is arranged very close to the field-of-view (FOV) and the size of the gradient system 6 is restricted by the need to keep the magnet size as small as possible, a problem results with the attainable linearity of the gradient fields over the extension of the imaging region containing the dental arches: either the maxilla, or the mandibula or both.

Figure 4:
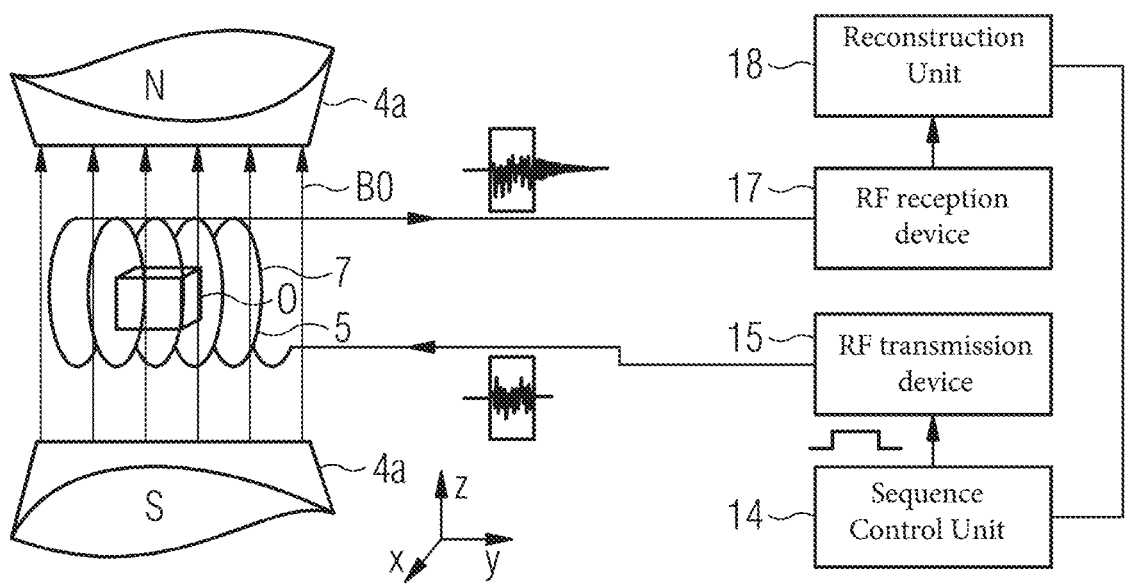
FIG. 4 shows the arrangement of a RF coil in a basic magnetic field according to the state of the art.

FIG. 4 shows the arrangement of an RF coil in a basic magnetic field B0 according to the state of the art (see also FIG. 1). An object O to be examined is surrounded by the coil of the RF transmission antenna system 5 that is also used as RF reception antenna system 7. RF signals are defined by the sequence control unit 14 and applied by the radio-frequency transmission device 15. The resulting signals to be measured are recorded by the radio-frequency reception device 17 and reconstructed by the reconstruction unit 18.

Figure 5:
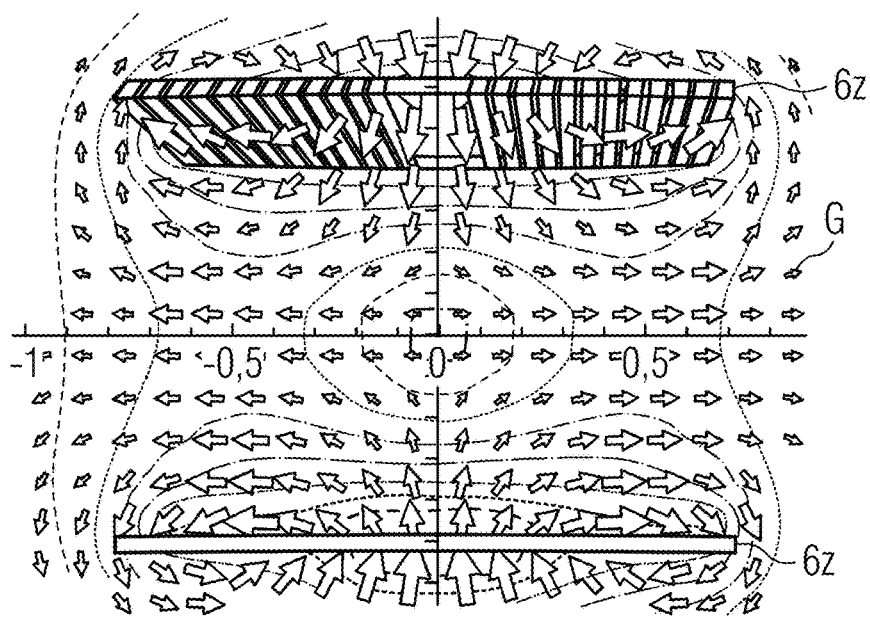
FIG. 5 shows the field of an exemplary pair of z-gradient coils in accordance with one or more embodiments of the present disclosure.

FIG. 5 shows the gradient field G of pair of exemplary Z-gradient coils 6z. The local magnetic field direction is shown by arrows, while the field strength is represented by the size of these arrows. It is evident that the Maxwell laws of physics prohibit the achievement of ideal parallel and linear gradient fields, especially within those spatial regions located very close to the gradient coils 6z.

Figure 6:
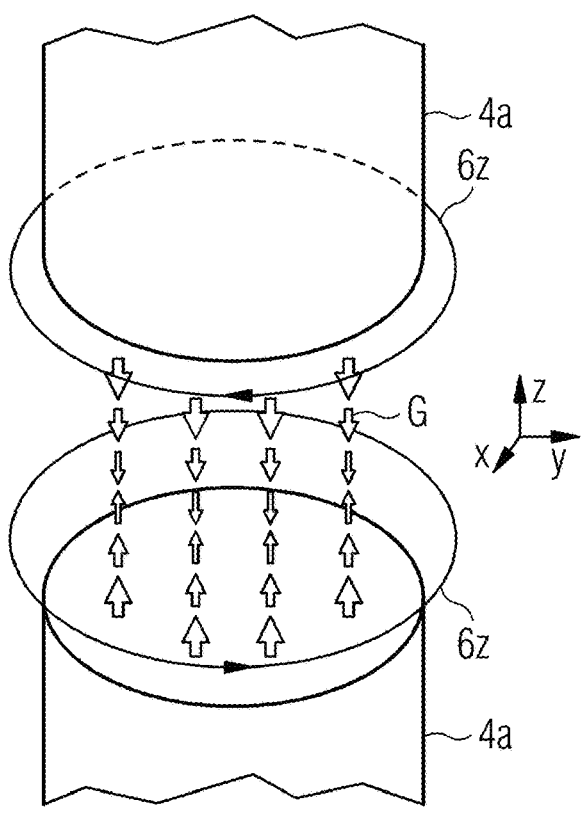
FIG. 6 shows an arrangement of gradient coils in accordance with one or more embodiments of the present disclosure.

FIG. 6 shows an arrangement of gradient coils 6z according to an embodiment of the disclosure. Around the magnet shoes 4a of a C-shaped basic field magnet 4 (see e.g. FIG. 2) a pair of gradient coils 6z is arranged. Between the two gradient coils 6z a gradient field G is shown that is effective along the Z-axis z, wherein the direction and strength is indicated with arrows. By looking more exactly at the field its field strength distribution would not be exactly linear but containing Maxwell and high-order, non-linear terms as depicted in FIG. 5.

Since the gradient coils 6z are arranged outside the basic magnetic field between the two magnet shoes 4, there will be a strongly reduced noise emission that can be diminished below hearing threshold depending on the arrangement of the gradient coils 6z outside the basic magnetic field.

Figure 7:
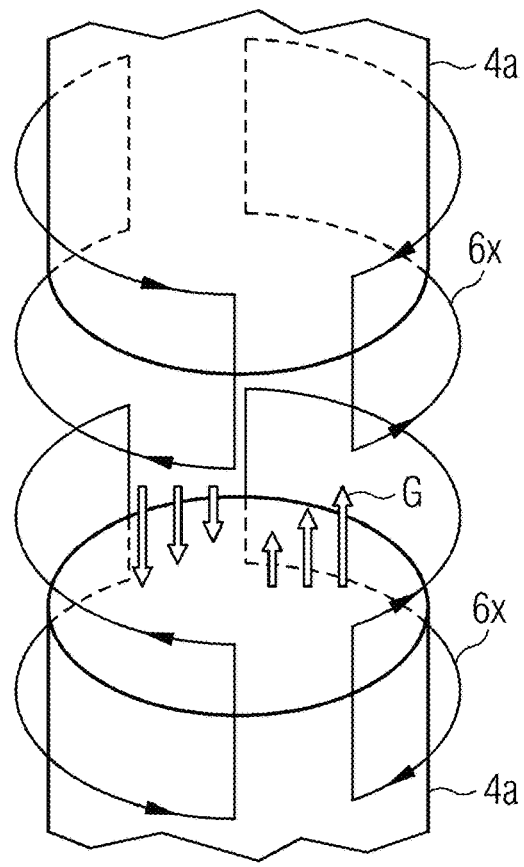
FIG. 7 shows an arrangement of gradient coils in accordance with one or more embodiments of the present disclosure.

FIG. 7 shows an arrangement of gradient coils according to an embodiment of the disclosure. The gradient coils 6x are arranged outside the basic magnetic field similar to FIG. 6 with the only difference that the two gradient coils 6z produce a gradient field G (indicated with arrows) that is effective along the x-axis x. If the arrangement would be turned for 90° around the z-axis z, the gradient coils would produce a gradient field that is effective along the y-axis y.

Figure 8:
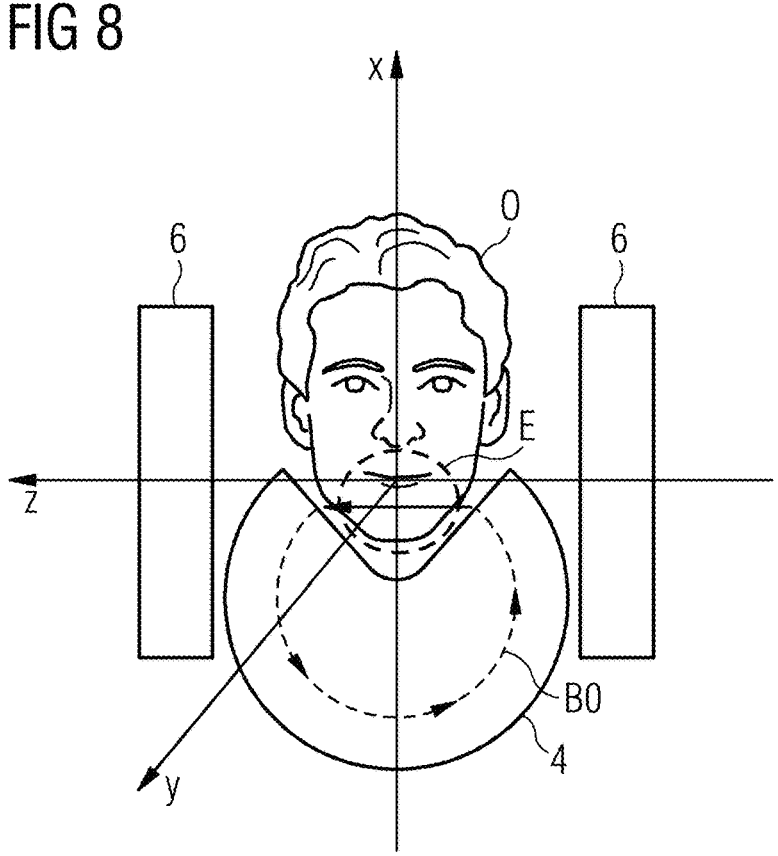
FIG. 8 shows an arrangement of a gradient system in accordance with one or more embodiments of the present disclosure with an open basic field magnet.

FIG. 8 shows an arrangement of a gradient system 6 according to an embodiment of the disclosure with an open basic field magnet 4. The gradient coil pairs of the gradient system 6, especially for generating gradient fields for all three axes x, y, z are arranged outside the basic magnetic field B0 of the basic field magnet 4. This has the main benefit that the linearity of the generated magnetic gradient fields can be maximized at least inside the examination area E (respective inside the FOV), whilst the geometry of the magnet can be optimized to fit the target anatomy. Thus, the size and finally the cost for the basic field magnet 4 can be significantly reduced for the same spatial extension of the examination area E. In addition, noise emission is also significantly reduced.

The gradient system 6 uses a pair of planar gradient coils e.g. in a parallel arrangement. A parallel coil arrangement compared to a V-shaped arrangement is here an advantageous architecture that achieves a better linearity of the gradient fields given relaxed design restrictions. These degrees of freedom can be further leveraged for minimizing the peripheral nerve stimulation effects and the generation of undesired eddy currents.

Figure 9:
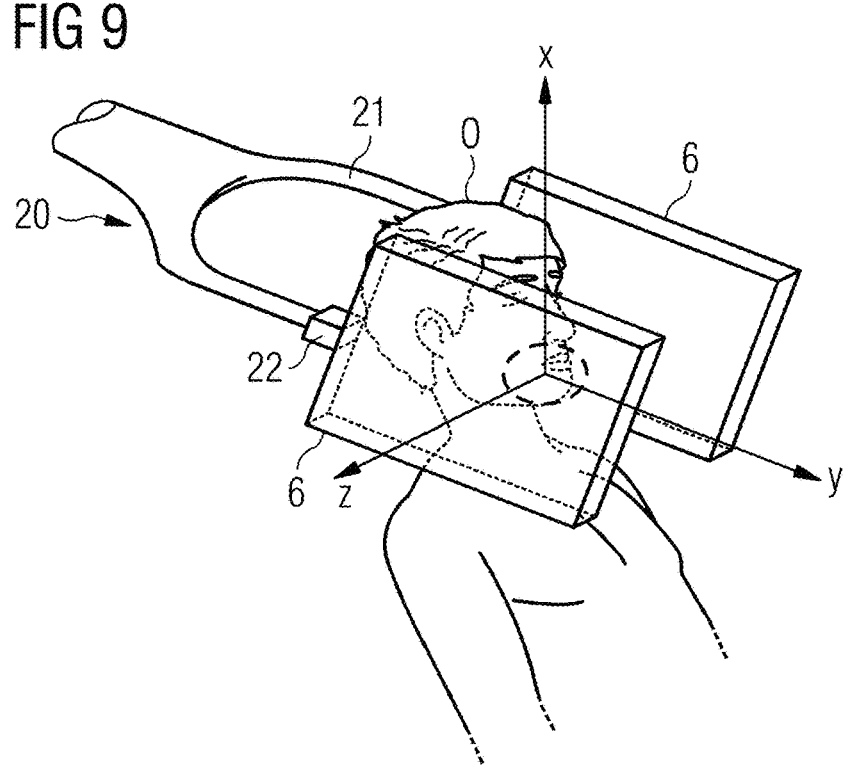
FIG. 9 shows an arrangement of a movable gradient system in accordance with one or more embodiments of the present disclosure.

FIG. 9 shows an arrangement of a movable gradient system 6 according to an embodiment of the disclosure. The gradient system uses planar gradient coils, while here no basic field magnet is shown due to a clearer picture. An arrangement of a basic field magnet 4 as shown in FIG. 8 for instance may be implemented here.

The gradient coil pairs of the gradient system 6 are placed symmetrically as related to the examination area E and at a distance therefrom. In the particular case of dental imaging, this solution allows for the patient head as examination object O to fit inside the space in between the coils of the gradient system 6.

In the shown advantageous geometry, the gradient coils are held by a positioning unit 20 comprising a forked actuator arm 21 with a motor 22 at the end of the forks, where the coils of the gradient system 6 are mounted such that they can be rotated at an angle around the z-axis z. As an example, the coils of the gradient system may also be shifted to each other along the Z-axis z. This allows to fit the gradient system 6 closer to the head and to avoid mechanical collisions with the patient shoulders.

As an example, the gradient coils are mechanically decoupled from the magnet and can be independently lifted-out by the actuator arm 21 during the non-imaging time and relocated away from the patient body. This approach further improves the access to the patient for the medical staff, as it may be often required for operative or non-operative dentistry or orthopedic procedures. The actuator arm (21) could be made of a soft magnetic material of high magnetic permeability to act as a yoke for the gradient fields. This will increase the efficiency of the gradient coils, reducing the peak currents, the heat development and the size and costs of the gradient system 6.

Figure 10:
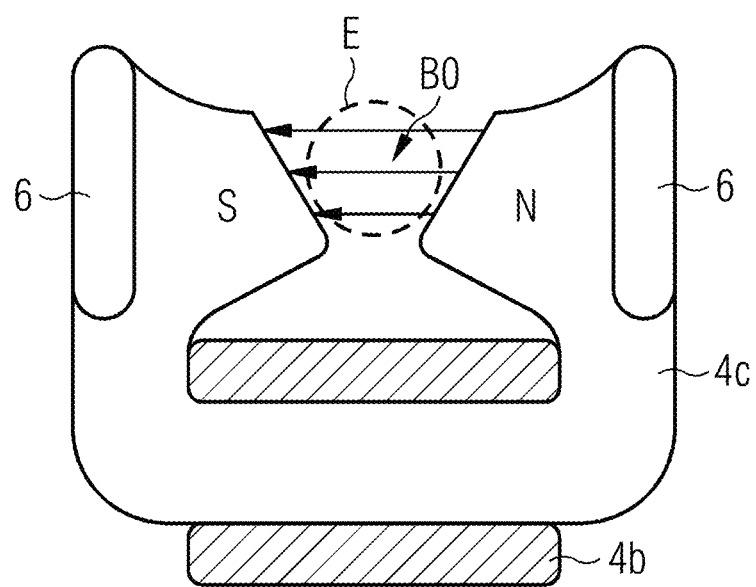
FIG. 10 shows an arrangement of a gradient system in accordance with one or more embodiments of the present disclosure combined with the yoke of a basic field magnet.

FIG. 10 shows an arrangement of a gradient system 6 according to an embodiment of the disclosure combined with the yoke 4c of a basic field magnet 4. A basic field magnet 4 with a basic field magnet coil 4b in the middle of a C-shaped yoke 4c is equipped with a gradient system 6 outside the basic magnetic field B0. As well, the basic field magnet coil 4b as the gradient system 6 use this iron yoke 4c to guide the magnetic flux lines toward the examination area E. The basic magnetic field B0 is generated by the current flowing into the basic field magnet coil 4b. The coils of the gradient system 6 reuse the same iron yoke 4c to efficiently guide and concentrate the gradient magnetic fields into the examination area E.

Figure 11:
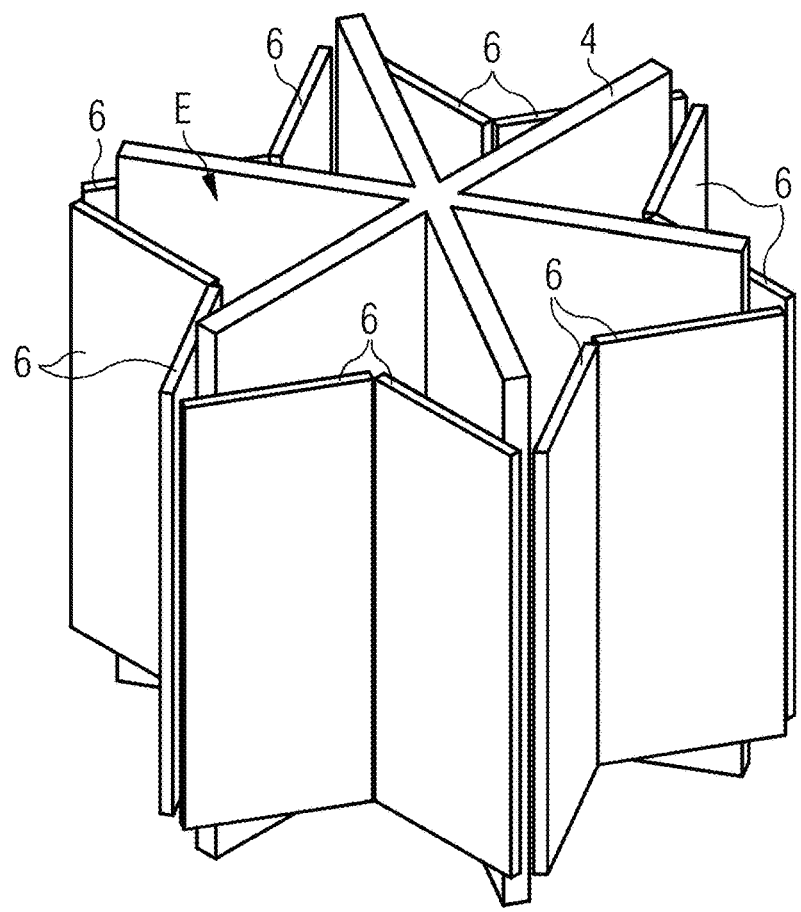
FIG. 11 shows a star shaped basic field magnet arrangement with a gradient system in accordance with one or more embodiments of the present disclosure.

FIG. 11 shows a star shaped basic field magnet 4 arrangement with a gradient system 6 arranged outside the area where the basic magnetic field is applied during an examination. To be more precise about the expression "outside", the coils of the gradient system 6 are arranged such that they are positioned in an area of significantly reduced magnetic field (stray field area) so that they are technically arranged outside the basic magnetic field that is used for examination.

A resulting magnetic resonance imaging system 1 would comprise here up to six examination areas E each equipped with a gradient system 6. The star-shaped arrangement of the coils of the basic field magnet 4 results in a toroidal basic magnetic field.

Figure 12:
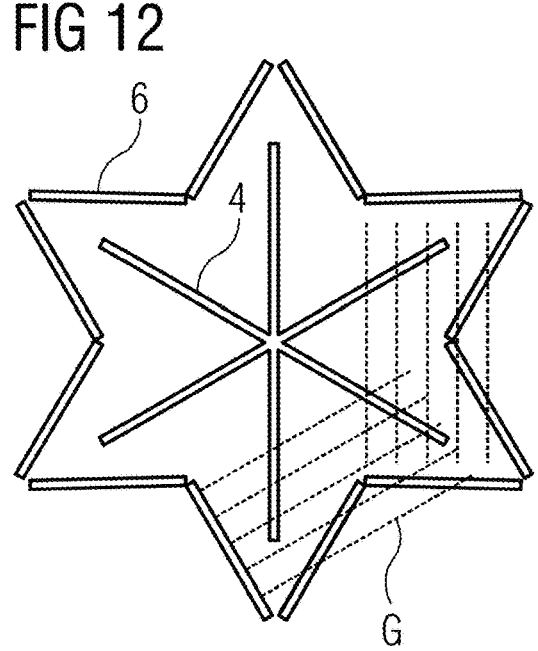
FIG. 12 shows the basic field magnet arrangement with the gradient system of FIG. 11 seen from above.

FIG. 12 is a sketch showing the device of FIG. 11 from above with two gradient fields G applied (dashed lines).

For an easy access of patients, the coils of the gradients can be arranged pivotably, so that they could open like doors to the examination areas. This has the advantage that the gradient system 6 could be used as blinds, as well.

Although the present disclosure has been disclosed in the form of preferred embodiments and variations thereon, it will be understood that numerous additional modifications and variations could be made thereto without departing from the scope of the disclosure. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

What is claimed is:

1. A magnet system for a magnetic resonance imaging system, comprising:
    a basic field magnet configured to generate a predefined basic magnetic field and having a shape configured to fit a predetermined anatomy of a patient to be examined via the magnetic resonance imaging system, the shape comprising a partial torus having a major radius and an open segment in accordance with an incomplete revolution of the major radius about an axis of revolution to provide the predefined basic magnetic field of the basic field magnet in a direction that is orthogonal to the axis of revolution of the partial torus; and
    a gradient system,
    wherein coils of the gradient system are positioned outside an area of the predefined basic magnetic field of the basic field magnet.

2. The magnet system according to claim 1, wherein the coils positioned outside the area of the predefined basic magnetic field of the basic field magnet are gradient coils for each of three coordinate axes, and comprise one of (i) shim coils, (ii) coils generating non-linear encoding fields, or (iii) dynamic field cycling coils for multi-dimensional spatial signal encoding and accelerated signal acquisition.

3. The magnet system according to claim 1, wherein the basic field magnet is a C-shaped magnet, and
    wherein the coils of the gradient system are arranged in a region of a pole shoe of the basic field magnet or such that the pole shoes of the basic field magnet lie between two of the coils of the gradient system.

4. The magnet system according to claim 1, wherein:
    the basic field magnet comprises a magnet yoke, and
    the coils of the gradient system are arranged such that a magnetic field of the coils of the gradient system couple into the magnet yoke,
    the distance between the magnet yoke and each one of the respective coils of the gradient system is less than 2 cm, and
    the coils of the gradient system are in contact with the magnet yoke.

5. The magnet system according to claim 1, wherein the coils of the gradient system are planar coils in a parallel arrangement.

6. The magnet system according to claim 1, wherein the coils of the gradient system are placed symmetrically relative to an examination area inside the predefined basic magnetic field of the basic field magnet.

7. The magnet system according to claim 1, wherein the coils of the gradient system are mechanically decoupled from the basic field magnet, and
    wherein the coils of the gradient system are movable relative to the basic field magnet via an actuator arm.

8. The magnet system according to claim 1, wherein the basic field magnet is arranged between the coils of the gradient system, and
    wherein a distance between the coils of the gradient system is larger than a dimension of the basic field magnet.

9. The magnet system according to claim 1, wherein the gradient system comprises a cooling system that is arranged outside the area of the predefined basic magnetic field of the basic field magnet.

10. A gradient system for a magnet system associated with a magnetic resonance imaging system, comprising:
    a basic field magnet configured to generate a predefined basic magnetic field and having a shape configured to fit a predetermined anatomy of a patient to be examined via the magnetic resonance imaging system, the shape comprising a partial torus having a major radius and an open segment in accordance with an incomplete revolution of the major radius about an axis of revolution to provide the predefined basic magnetic field of the basic field magnet in a direction that is orthogonal to the axis of revolution of the partial torus;
    a first pair of coils;
    a second pair of coils; and
    a third pair of coils,
    wherein each of the first, second, and third pair of coils is (i) configured to be independently controlled to switch their respective gradients in one of an x-direction, a y-direction, or a z-direction, and (ii) arranged outside an area of the predefined basic magnetic field associated with the basic field magnet, and
    wherein the x-direction, the y-direction, and the z-direction are each perpendicular to one another.

11. A magnetic resonance imaging system, comprising:
    a magnetic resonance scanner; and
    a magnet system including:
        a basic field magnet configured to generate a predefined basic magnetic field and having a shape configured to fit a predetermined anatomy of a patient to be examined via the magnetic resonance imaging system, the shape comprising a partial torus having a major radius and an open segment in accordance with an incomplete revolution of the major radius about an axis of revolution to provide the predefined basic magnetic field of the basic field magnet in a direction that is orthogonal to the axis of revolution of the partial torus; and
        a gradient system,
        wherein coils of the gradient system are positioned outside an area of the predefined basic magnetic field of the basic field magnet.

* * * * *